United States Patent [19]
Davé

[11] Patent Number: 5,517,301
[45] Date of Patent: May 14, 1996

[54] APPARATUS FOR CHARACTERIZING AN OPTIC

[75] Inventor: Sandeep Davé, Bethel, Conn.

[73] Assignee: Hughes Aircraft Company, Los Angeles, Calif.

[21] Appl. No.: 97,427

[22] Filed: Jul. 27, 1993

[51] Int. Cl.$^6$ .................................................. G01N 21/32
[52] U.S. Cl. ...................................... 356/239; 250/559.42
[58] Field of Search ............................... 356/239, 237, 356/338, 240, 244, 128, 133–137, 429–431, 440, 73.1; 250/223 B, 227.23, 227.29, 227.21, 561, 562, 571, 572, 559.42, 559.48, 559.49

[56] References Cited

U.S. PATENT DOCUMENTS

| H376 | 12/1987 | Bremer | 356/239 |
|---|---|---|---|
| 3,460,893 | 8/1969 | Wilks, Jr. | 356/429 |
| 3,737,665 | 6/1973 | Nagae | 356/239 |
| 3,988,068 | 10/1976 | Sprague | 356/239 |
| 4,297,032 | 10/1981 | Temple | 356/239 |
| 4,401,893 | 8/1983 | Dehuysser | 356/239 |
| 4,456,374 | 6/1984 | Langberg | 356/237 |
| 4,481,450 | 11/1984 | Watanabe et al. | 318/444 |
| 4,808,813 | 2/1989 | Champetier | 250/227.23 |
| 5,152,600 | 10/1992 | Boring | 356/239 |
| 5,196,901 | 3/1993 | Champetier | 356/338 |

FOREIGN PATENT DOCUMENTS

| 0461424 | 12/1991 | European Pat. Off. | 356/371 |
|---|---|---|---|
| 1950847 | 4/1971 | Germany | 356/239 |
| 0044587 | 4/1979 | Japan | 356/239 |

Primary Examiner—Hoa Q. Pham
Attorney, Agent, or Firm—W. C. Schubert; W. K. Denson-Low

[57] ABSTRACT

An apparatus (10) for characterizing an optic (14) includes a light source (20) adapted to direct a light beam into an optic (14) such that total internal reflection of the light beam occurs. A light detector (38) is disposed to detect light exiting the optic (14). The apparatus (10) also includes a reservoir for holding and dispensing an index of refraction matching fluid between the optic (14) and the light detector (38) to enable light to exit the optic (14) toward the light detector (38) such that the material of the optic (14) is characterized rather than merely the surface thereof.

19 Claims, 1 Drawing Sheet

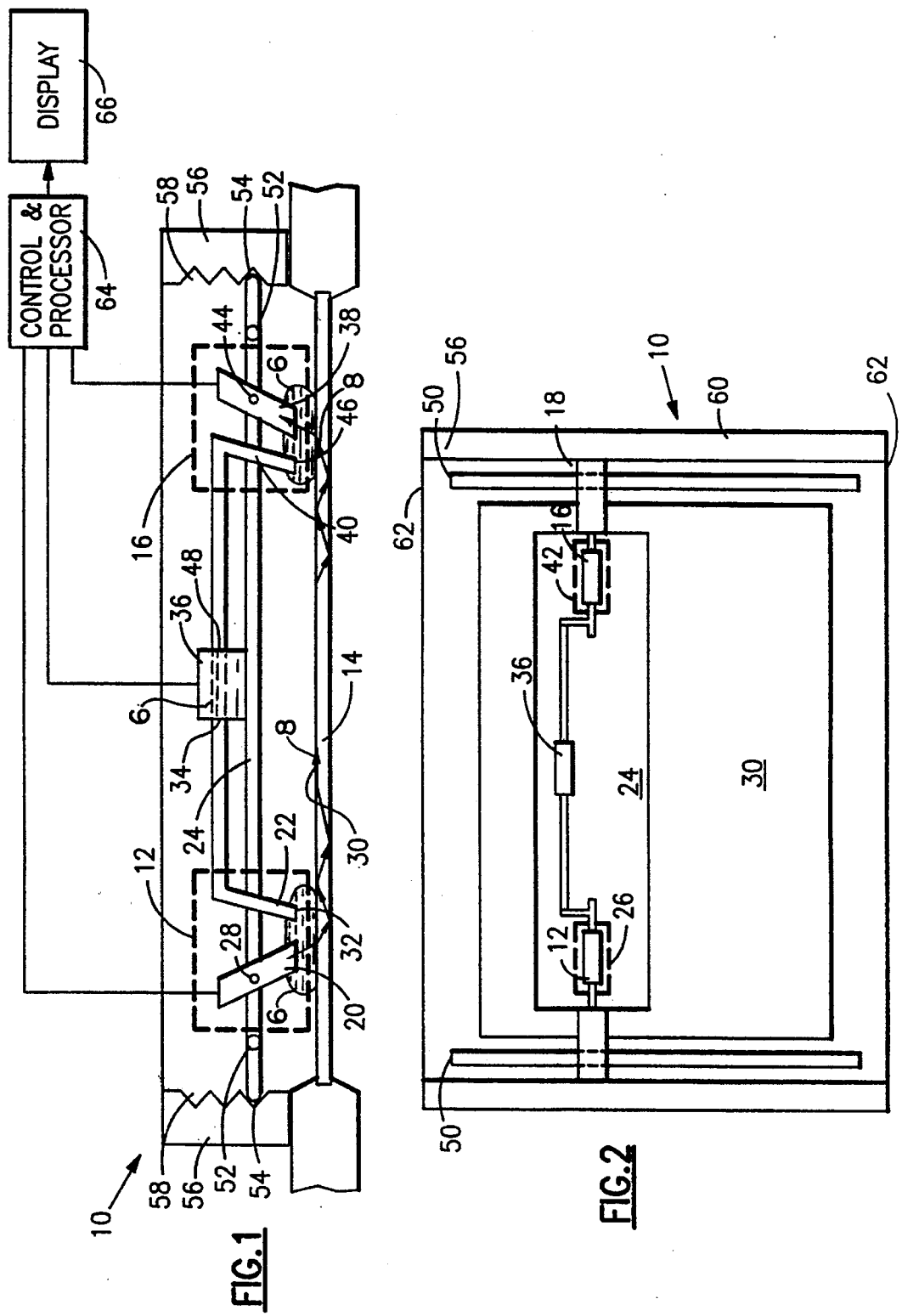

APPARATUS FOR CHARACTERIZING AN OPTIC

BACKGROUND OF THE INVENTION

The present invention generally relates to an apparatus for characterizing an optic and, in particular, relates to one such apparatus wherein a light beam is directed toward an optic at an angle that ensures total internal reflection of the light within the optic.

There are many techniques for characterizing optical elements. For example, many optics can be readily characterized by the use of interferograms. Such interferometric techniques are well known in the field of optics and a detailed discussion is not believed necessary herein. As is well known, however, interferograms generally provide useful information only about the surface of the optic being examined. Hence, such techniques are not beneficial when the optic being characterized is a window. Further, because of the complexity of the equipment involved, interferometry is not a technique readily adaptable for characterizing an optic once that optic has been installed and is in use.

Currently, in the case of characterizing an optical window, particularly characterizing such a window in-situ, an instrument that directs a light beam of a single visible wavelength is available. Such an instrument measures the direct scattered light from the surface of the optic being characterized. One such instrument is portable and hence can be used to characterize optics both before and after the optic is installed and used.

However, such an instrument has a number of significant drawbacks. The primary drawback is that only the surface of the optic is characterized. The current instruments do not provide information about the internal integrity of the optic. In addition, the single wavelength limitation of such instruments limits the usefulness of such instruments since the particular wavelength available may not be indicative of the performance of the optic being characterized. This is particularly true in cases where the optic being characterized has different coatings on the surfaces thereof. Further, such instruments usually only characterize a relatively small area of the surface of the optic. This limitation is a result of the relatively small spot sized provided by the available instruments. Hence, in order to characterize an entire optical surface, the spot would have to be moved over each point of the surface. Such an analysis would be quite time consuming.

Consequently, there is a considerable need for an apparatus for characterizing an optic that overcomes the above-recited drawbacks of conventional apparatus.

SUMMARY OF THE INVENTION

Accordingly, it is one object of the present invention to provide an apparatus for characterizing an optic that does not exhibit the above-recited drawbacks.

This object is accomplished, at least in part, by an apparatus for characterizing an optic that provides a light beam that is totally internally reflected within the optic to thereby provide a characterization of the material of the optic.

Other objects and advantages of the present invention will become apparent to those skilled in the art from the following detailed description read in conjunction with the appended claims and the drawings attached hereto.

BRIEF DESCRIPTION OF THE DRAWINGS

The drawings, not drawn to scale, include:

FIG. 1 which is a schematic side view of an apparatus for characterizing an optic embodying the principles of the present invention; and FIG. 2 which is a schematic top view of the apparatus embodying the principles of the present invention.

DETAILED DESCRIPTION OF THE INVENTION

An apparatus, generally indicated at 10 in the drawings and embodying the principles of the present invention, includes means 12 for introducing a light beam into an optic 14 to be characterized such that the light beam 8 in totally internally reflected within the optic 14, means 16, spaced apart from the means 12 for introducing a light beam into the optic 14, for detecting light exiting the optic 14, and means 18 for translating the light introducing means 12 and the light detecting means 16 across the optic 14.

In the preferred embodiment, the means 12 for introducing a light beam in the optic 14 includes a light source 20 and a means 22 for dispensing an index of refraction matching fluid 6 between the light source 20 and the optic 14. Preferably, the angle of the light 8 source 20 is adjusted so that light 8 entering the optic 14 from the light 8 source 20 is totally internally reflected within the optic 14. In one embodiment, the light source 20 is mounted on a base member 24 and extends through a first elongated opening 26 in the base member 24. The light source 20 can be mounted, for example, on a pin 28 about which the light source 20 can be rotated to adjust the angle of the light beam emanating therefrom with respect to the surface 30 of the optic 14. In addition, the light source 20 is mounted so that it can be moved along the elongated opening 26 to adjust the position thereof with respect to the surface 30 of the optic 14. The light source 20 can be either a broadband light source or a single wavelength light source depending upon the particular optic 14 being characterized.

For example, if the optic has different coatings, it may be desirable to use a broadband light source having multiple wavelengths for analyzing the internal characteristics of the optic.

Preferably, the means 22 for dispensing an index of refraction matching fluid is a fluid 6 conduit, such as a length of tubing, having a first end 32 disposed proximate the light source 20 and a second end 34 connected to an index of refraction matching fluid reservoir 36 for holding a preselected volume of index of refraction matching fluid. In one particular embodiment, the fluid conduit is a length of plastic tubing having an inside diameter of about 1/16th of an inch. In one embodiment, the fluid reservoir 36 is an electrically controlled pump that dispenses the index of refraction matching fluid in response to can electrical signal. Alternatively, the fluid reservoir 36 an be a hand operated dispenser similar to a conventional eye dropper.

The means 16 for detecting light includes a light detector 38 and a means 40 for dispensing an index of refraction matching fluid 6 between the light detector 38 and the optic 14. Preferably, the angle of the light 8 detector 38 is adjusted so that light 8 exiting the optic 14 is directed into the light detector 38. In one embodiment, the light detector 38 is mounted on the base member 24 and extends through a second elongated opening 42 in the base member 24. Preferably, the second elongated opening 42 is laterally aligned with the first elongated opening to ensure that the light detector 38 receives the maximum light exiting the optic. Similarly, the light detector 38 can be mounted, for example, on a pin 44 about which the light detector 38 can be rotated to adjust the angle thereof with respect to the surface 30 of the optic 14. In addition, the light detector 38 is mounted so that it can be moved along the second elongated opening 42 to adjust the position thereof with respect to the surface 30 of the optic 14. Although many light detectors are readily available, it is preferred that the light detector 38 be of the type that outputs an electrical signal proportional to the intensity of the light detected.

Preferably, the means 40 for dispensing an index of refraction matching fluid is a fluid conduit, such as a length of tubing, having a first end 46 disposed proximate the light detector 38 and a second end 48 connected to the index of refraction matching fluid reservoir 36 for holding a preselected volume of index of refraction matching fluid 6. Alternatively, the means 16 for detecting light can have a separate source of index of refraction matching fluid. As with the means 22, in this embodiment, the conduit is a length of plastic tubing having an inside diameter of about 1/16th of an inch.

In one particular embodiment, the means 18 for translating the means 12 for introducing light and the means 16 for detecting light includes a pair of rails 50. Preferably, the rails 50 are parallel. The rails 50 extend through corresponding openings 52 in the base member 24. Preferably, the openings 52 in the base member 24 are proximate the ends 54 thereof to enable the characterization of wide optics. Typically, the openings 52 in the base member 24 can be sized to allow the frictional fit of the rails 50 therethrough. Alternatively, a conventional locking mechanism can be employed to fix the position of the base member 24 during operation.

In the embodiment shown in the Figures, the base member 24 is disposed within a housing 56 having notches 58 along a first pair of opposing sides 60 thereof. Preferably, the ends 54 of the base member 24 are sized to ride within the notches 58 to enable translation of the base member 24 along the rails 50. Further, the notches 58 are disposed to retain the base member 24 at a particular distance above the surface 30 of the optic 14.

In the embodiment shown, the opposing notched sides 60 of the housing 56 are secured at the ends thereof by a second pair of opposing sides 62. Preferably, the first and second pairs of opposing sides, 60 and 62, respectively, have a height that is selected to prevent extraneous light from impinging upon the optic 14 during the characterization thereof. Further, the first and second pairs of opposing sides, 60 and 62, respectively, are either sized for each particular optic, or window, to be characterized or are made adjustable to accommodate various sizes of optics 14. The first pair of opposing sides 60, in one specific embodiment, are fabricated from a semi-rigid material such as rubber to enable the housing 56 to conform to the surface 30 of the optic 14 being characterized. If needed the second pair of opposing sides 62 can also be semi-rigid to allow the housing 56 to conform to any curvature along the width of the surface 30. The first and second pairs, 60 and 62, respectively, of opposing sides of the housing 56 thus allow a light tight fit for the optic 14 to be characterized.

In the preferred embodiment, the light source 20, the light detector 38 and the reservoir 36 are electrically connected to and controlled by a preprogrammed microprocessor 64. The microprocessor 64 is connected to a signal display 66, such as a video display, for displaying the output signal.

In operation, for example in characterizing of a window installed in an aircraft, the housing 56 is adjusted for the size of the window and the curvature, if any, of the aircraft. The housing 56 is then placed against the aircraft and the means 12 for introducing light and the means 16 for detecting light are laterally adjusted proximate the edges of the window. The light source 20 is adjusted to ensure the total internal reflection of the light beam 8 emanating therefrom within the optic 14. This adjustment is determined by conventional optical analysis taking into account such factors as the material of the window, whatever coatings are on the window as well as the presence of the index of refraction matching fluid 6. The light detector 38 is adjusted to receive light from the optic 14. The reservoir then dispenses index of refraction matching fluid 6 and a measurement is taken. The light 8 introduced into the optic 14 is totally internally reflected between the surfaces of the optic 14 and propagates between the light source 20 and the light detector 38. The index of refraction matching 6 fluid between the light detector 38 and the optic 14 causes the boundary conditions to change such that the light exits the optic 14 and impinges upon the light 8 detector 38. Because the light beam 8 traverses the volume of the optic 14, rather than just the surface 30, any internal defects, as well as any surface defect of the optic 14, causes light scattering. Such light scattering causes less light to reach the light detector 38. Hence, the amount of light reaching the light detector 38 is indicative of the integrity of the entire window material.

The base member 24 is translated along the optic 14 subsequent to each measurement. The measurements are compared to known, or empirically generated data by the microprocessor 64 and the results are displayed on the display 66. By comparing the measurements of the optic 14 in-situ to a known standard, the light transmission of the entire volume of the optic 14 is characterized.

Although the present invention has been described by use of one or more particular embodiments, it will be understood by those skilled in the art that other configurations or arrangements can also be implemented without departing from the spirit and scope hereof. Hence, the present invention is deemed limited only by the appended claims and the reasonable interpretation thereof.

What is claimed is:

1. An apparatus for characterizing an optic in-situ, comprising:

means for introducing a light beam into an optic to be characterized through a surface thereof such that said light beam is totally internally reflected within said optic;

means for detecting light exiting through said surface of said optic, said means for detecting light outputting a signal related to the intensity of said light detected; and means for comparing said signal with a known signal level indicative of a standard optic such that the integrity of the entire material of said optic is characterized.

2. The apparatus as claimed in claim 1 wherein said means for introducing a light beam includes:

a light source; and means for dispensing an index of refraction matching fluid between said light source and said optic.

3. The apparatus as claimed in claim 2 wherein said light source is a broadband light source.

4. The apparatus as claimed in claim 2 wherein said light source is a single wavelength light source.

5. The apparatus as claimed in claim 2 wherein said means for dispensing an index of refraction matching fluid between said light source and said optic includes:

a fluid conduit having one end disposed proximate said light source and communicating with a reservoir of index of refraction matching fluid.

6. The apparatus as claimed in claim 5 where said means for dispensing an index of refraction matching fluid between said light source and said optic includes:

a fluid conduit having one end disposed proximate a said light source and communicating with a reservoir of index of refraction matching fluid.

7. The apparatus as claimed in claim 2 wherein said means for detecting light includes:

a light detector;

means for dispensing an index of refraction matching fluid between said light detector and said optic.

8. The apparatus as claimed in claim 7 wherein said light detector outputs a signal proportional to the intensity of the light impinging thereon.

9. The apparatus as claimed in claim 1 further including:

means for translating said light introducing means and said light detecting means across said optic.

10. The apparatus as claimed in claim 9 wherein said translating means includes:

a base member, said means for introducing light and said means for detecting light being mounted on said base member having openings proximate the ends thereof; and a pair of rails, said rails extending through said openings of said base member.

11. The apparatus as claimed in claim 10 further including:

a housing, said housing having a first and a second pair of opposing sides, said first pair of opposing sides having means for retaining said base member.

12. The apparatus as claimed in claim 11 wherein said retaining means includes a plurality of notches sized to receive said base member.

13. The apparatus as claimed in claim 1 further comprising:

microprocessor for controlling said means for introducing light and means for detecting light and for processing said signal from said means for detecting light.

14. The apparatus as claimed in claim 13 further including:

means coupled to said processing means for displaying information relative to the characterization of said optic.

15. An apparatus for characterizing an optic in-situ comprising:

a base member;

a light source connected to said base member and disposed proximate said optic for injecting light in said optic through a surface thereof;

a light detector connected to said base member and disposed proximate said optic for receiving light from said optic through said surface thereof to provide a detected signal related to the intensity of light detected;

means for dispensing an index of refraction matching fluid between said light source and said optic and said light detector and said optic; and a microprocessor for controlling said light detector, said light source, and said dispensing means and for processing said detected signal to provide a characterization of the integrity of the entire material of said optic.

16. The apparatus of claim 15 said microprocessor for controlling the angle of the source and detector relative to a surface of the optic.

17. The apparatus of claim 15 further comprising means for translating said base member across said optic, said microprocessor receiving a plurality of detected signals to characterize the entire volume of the optic.

18. The apparatus of claim 17 further comprising a housing coupled to said base member, said housing including said translating means, and wherein said housing including adjustable means for reconfiguring said apparatus for characterizing different sized optics.

19. The apparatus of claim 15 wherein said light source is a broadband light source.

\* \* \* \* \*